US007920674B2

(12) United States Patent
Kang et al.

(10) Patent No.: US 7,920,674 B2
(45) Date of Patent: Apr. 5, 2011

(54) APPARATUS AND METHOD FOR IMAGE PROCESSING

(75) Inventors: Dong-Goo Kang, Suwon-si (KR); Young Hun Sung, Hwaseong-si (KR); Jong Ha Lee, Hwaseong-si (KR); Sung Su Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 43 days.

(21) Appl. No.: 12/461,555

(22) Filed: Aug. 14, 2009

(65) Prior Publication Data

US 2010/0091943 A1    Apr. 15, 2010

(30) Foreign Application Priority Data

Oct. 10, 2008  (KR) ......................... 10-2008-0099871
Feb. 24, 2009  (KR) ......................... 10-2009-0015133

(51) Int. Cl.
*G01N 23/04*   (2006.01)

(52) U.S. Cl. ...................................... 378/62; 378/98.12
(58) Field of Classification Search ..................... 378/62, 378/82, 84, 98.11, 98.12, 156–159; 382/130–132
See application file for complete search history.

(56) References Cited

FOREIGN PATENT DOCUMENTS

| KR | 10-2003-0031822 | 4/2003 |
| KR | 10-2008-0042806 | 5/2008 |
| WO | 02/28154 A1 | 4/2002 |

*Primary Examiner* — Courtney Thomas
(74) *Attorney, Agent, or Firm* — Staas & Halsey LLP

(57) ABSTRACT

An image processing apparatus and an image processing method. The image processing apparatus includes an image obtaining unit to obtain a plurality of X-ray images using a plurality of X-rays corresponding to each of a plurality of energy bands being different from each other, a first processing unit to generate a plurality of material images using the plurality of X-ray images, and a second processing unit to generate a high contrast X-ray image using at least one of the plurality of material images.

21 Claims, 14 Drawing Sheets
(2 of 14 Drawing Sheet(s) Filed in Color)

20keV

25keV

30keV

40keV

FAT

WATER

PROTEIN

BONE

APPARATUS AND METHOD FOR IMAGE PROCESSING

CROSS-REFERENCE TO RELATED APPLICATIONS

This application claims the benefit of Korean Patent Application No. 10-2008-0099871, filed on Oct. 10, 2008, and No.10-2009-0015133, filed on Feb. 24, 2009, in the Korean Intellectual Property Office, the disclosures of which are incorporated herein by reference.

BACKGROUND

1. Field

Example embodiments of the present disclosure relate to an apparatus and method for image processing, and more particularly, to an apparatus and method for image processing which may obtain material images, characteristic images, and anatomical images using a plurality of X-ray images corresponding to multiple monochromatic bands.

2. Description of the Related Art

An X-ray has been utilized in industrial and medical applications for various purposes such as image photographing for medical use, image photographing for security inspection, non-destructive tests, and the like since having been discovered by Roentgen in 1895.

Since each material has a unique attenuation coefficient with respect to the X-ray, a strength of the X-ray may be sensed by measuring penetration to obtain an X-ray image. Hard tissue such as bones of a human body, metals, and the like may have great X-ray absorptance, and soft tissues such as water, fat, and the like may have relatively less X-ray absorptance.

In addition, different X-ray absorptances for each material may be shown depending on an energy band also referred to as a wavelength. In general, when an energy band of the X-ray is low, a difference between the X-ray absorptances for each material may be great, and when the energy band thereof is high, the difference therebetween may be relatively less.

An existing X-ray image may use a polychromatic X-ray having a wide energy band. Accordingly, in the X-ray image, a contrast of the hard tissues may be relatively high, however, the contrast of the soft tissues may be relatively low. Also, a thickness of a material through which the X-ray is penetrated may affect the X-ray image.

Thus, a need exists for X-ray images featuring a high contrast with respect to the soft tissues as well as the hard tissues.

SUMMARY

One or more example embodiments may provide an image processing apparatus and method which may generate a high contrast X-ray image in which a contrast with respect to soft tissues as well as hard tissues is improved.

One or more example embodiments may also provide an image processing apparatus and method which may obtain an X-ray image divided for each material, and perform an image processing based on the obtained X-ray image, thereby generating characteristic images or anatomical images.

According to example embodiments, an image processing apparatus may be provided. The image processing apparatus may include an image obtaining unit to obtain a plurality of X-ray images using a plurality of X-rays corresponding to each of a plurality of energy bands being different from each other, a first processing unit to generate a plurality of material images using the plurality of X-ray images, and a second processing unit to generate a high contrast X-ray image using at least one of the plurality of material images.

In this instance, according to an example embodiment, the image obtaining unit may include an X-ray generation unit to generate a polychromatic X-ray, a filtering unit to filter the polychromatic X-ray to provide the plurality of X-rays corresponding to each of the plurality of energy bands, and an X-ray sensing unit to sense the plurality of X-rays corresponding to each of the plurality of energy bands passing through the filtering unit to thereby obtain the plurality of X-ray images.

According to another example, the image obtaining unit may include an X-ray generation unit to generate a polychromatic X-ray, a spectroscopic unit to refract the polychromatic X-ray to thereby divide the refracted polychromatic X-ray into the plurality of X-rays corresponding to each of the plurality of energy bands, and an X-ray sensing unit to sense the plurality of X-rays corresponding to each of the plurality of energy bands passing through the spectroscopic unit to thereby obtain the plurality of X-ray images.

According to another example embodiment, the image obtaining unit may include an X-ray generation unit to generate a polychromatic X-ray, and an X-ray sensing unit to obtain the plurality of X-ray images corresponding to each of the plurality of energy bands using the polychromatic X-ray.

Also, the first processing unit may select at least m X-ray images, m being a natural number, from among the plurality of X-ray images, and analyze the selected m X-ray images in a pixel unit to generate m material images.

Also, the second processing unit may perform an independent component analysis using a pixel value of at least two material images from among the m material images to thereby obtain at least one independent component image, and combine the independent component images to thereby obtain the high contrast X-ray image.

Also, the second processing unit may perform at least one post processing of a noise reduction, a contrast adjustment, and an edge enhancement before performing the independent component analysis.

Also, according to another example embodiment, the second processing unit may generate a characteristic image in which an outlier part is identified, using at least two material images from among the m material images, the outlier part being a part in which a ratio between materials is outside a known normal range.

Also, the m material images may include a water image, a fat image, a protein image, and an ash image.

In this instance, the second processing unit may identify a part in which a ratio of water and fat is outside a known normal range as an outlier part using the water image and the fat image, and discriminate at least one of a color and shade of the outlier part from other parts to thereby generate a characteristic image.

According to other example embodiments, an image processing apparatus may be provided. The image processing apparatus may include an image obtaining unit to obtain a plurality of X-ray images using a plurality of X-rays corresponding to each of a plurality of energy bands being different from each other, and a third processing unit to perform an independent component analysis using a pixel value of at least two X-ray images from among the plurality of X-ray images to thereby obtain at least one independent component image, and to combine the at least one independent component image to thereby generate a high contrast X-ray image.

According to still other example embodiments, an image processing method may be provided. The image processing method may include obtaining a plurality of X-ray images using a plurality of X-rays corresponding to each of a plurality of energy bands being different from each other, generating a plurality of material images using the plurality of X-ray images, and generating a high contrast X-ray image using at least one of the plurality of material images.

In this instance, the obtaining may include generating a polychromatic X-ray, filtering the polychromatic X-ray to provide the plurality of X-rays corresponding to each of the plurality of energy bands, and sensing a plurality of X-rays corresponding to each of the filtered plurality of energy bands to obtain the plurality of X-ray images.

Also, the generating of the plurality of material images may include selecting at least m X-ray images, m being a natural number, from among the plurality of X-ray images, and analyzing the selected at least m X-ray images in a pixel unit to generate m material images.

Also, the generating of the high contrast X-ray image may include performing an independent component analysis using a pixel value of at least one material image from among the generated m material images, and combining at least one independent component image obtained through the independent component analysis to generate the high contrast X-ray image.

Also, according to another example embodiment, the generating of the high contrast X-ray image may include calculating an abnormality of a part in which a ratio between materials is outside a known normal range, using at least two material images from among the generated m material images, and adjusting a color or brightness value of the calculated outlier part to obtain an image identified as the outlier part.

Also, the m material images may include a water image, a fat image, a protein image, and an ash image.

In this instance, the generating of the high contrast X-ray image may include detecting an outlier part in which a ratio of water and fat is outside a known normal range using the water image and the fat image, and adjusting a color and brightness value of the detected outlier part to generate an image identified as the outlier part.

According to yet other example embodiments, an image processing method may be provided. The image processing method may include obtaining a plurality of X-ray images using a plurality of X-rays corresponding to each of a plurality of energy bands, performing an independent component analysis using pixel values of at least two X-ray images from among the obtained plurality of X-ray images, and combining at least two independent component images obtained through the independent component analysis to thereby generate a high contrast X-ray image.

Additional aspects and/or advantages will be set forth in part in the description which follows and, in part, will be apparent from the description, or may be learned by practice of the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects and advantages will become apparent and more readily appreciated from the following description of the embodiments, taken in conjunction with the accompanying drawings of which.

DETAILED DESCRIPTION

Figure 1:
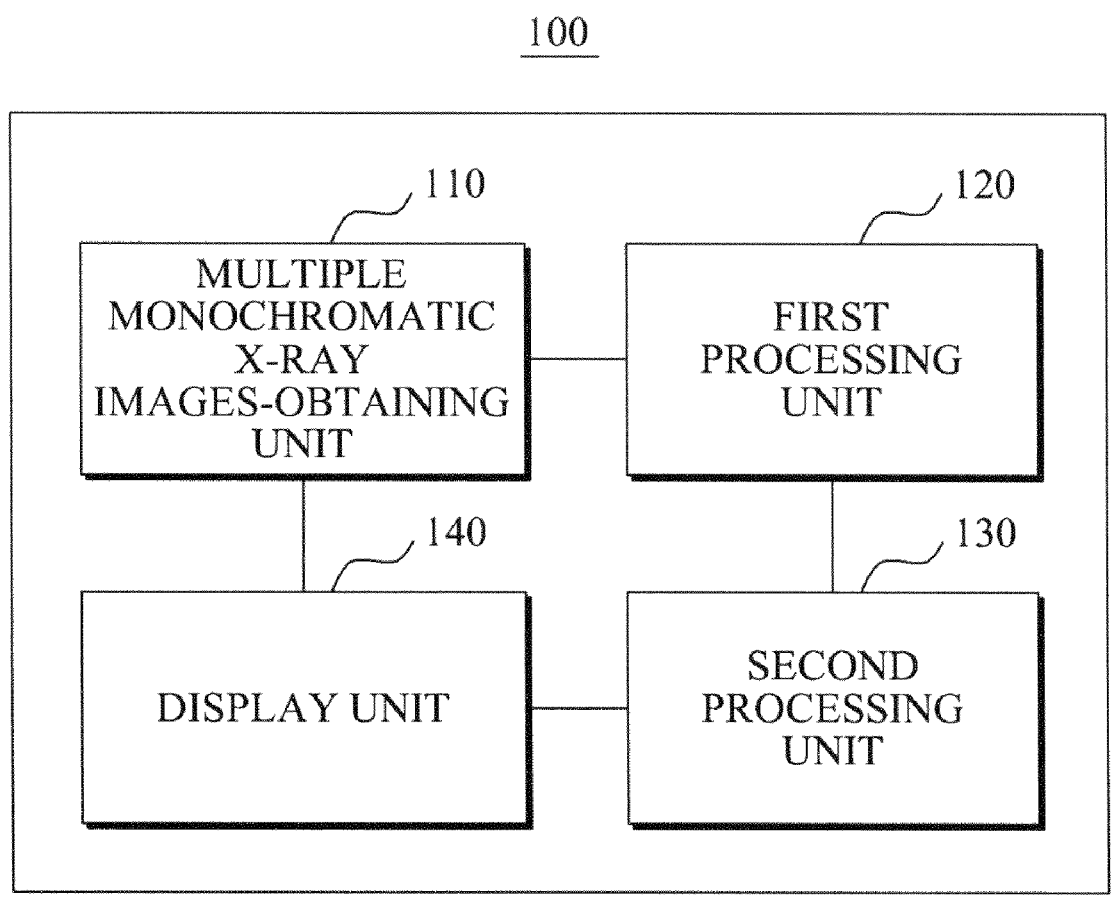
FIG. 1 illustrates an image processing apparatus according to example embodiments.

Reference will now be made in detail to example embodiments, examples of which are illustrated in the accompanying drawings, wherein like reference numerals refer to the like elements throughout. Example embodiments are described below to explain the present disclosure by referring to the figures.

FIG. 1 illustrates an image processing apparatus 100 according to example embodiments.

The image processing apparatus 100 includes an image obtaining unit 110, a first processing unit 120, a second processing unit 130, and may further include a display unit 140.

The image obtaining unit 110 may obtain a plurality of X-ray images using an X-ray corresponding to each of a plurality of energy bands being different from each other.

According to an example embodiment, the image obtaining unit 110 may include an X-ray generation unit to generate a polychromatic X-ray, a filtering unit to filter the polychromatic X-ray to provide an X-ray corresponding to each of the plurality of energy bands, and an X-ray sensing unit to sense an X-ray corresponding to each of the plurality of energy bands passing through the filtering unit to thereby obtain the plurality of X-ray images.

However, according to another example embodiment, the image obtaining unit 110 may include an X-ray generation unit to generate a polychromatic X-ray, a spectroscopic unit to refract the polychromatic X-ray to thereby divide the refracted polychromatic X-ray into a plurality of X-rays corresponding to each of the plurality of energy bands, and an X-ray sensing unit to sense the plurality of X-rays corresponding to each of the plurality of energy bands passing through the spectroscopic unit to thereby obtain the plurality of X-ray images.

Also, according to another example embodiment, the image obtaining unit 110 may include an X-ray generation unit to generate a polychromatic X-ray, and an X-ray sensing unit to obtain a plurality of X-ray images corresponding to each of the plurality of energy bands using the polychromatic X-ray.

As an example of the X-ray sensing unit, a photon counting X-ray detector may be given. The photon counting X-ray detector may include an X-ray detector and a read-out circuit connected with each other through bump bonding.

In this instance, the X-ray detector to which a reverse voltage is applied may generate an electron-hole pair (EHP) through a reaction with an entering X-ray, and a generated electric charge may be transmitted to a preamplifier of the read-out circuit to thereby output a voltage signal corresponding to the generated electric charge.

Then, the voltage signal outputted in the preamplifier may be transmitted to a comparator, and the transmitted voltage signal may be compared with an arbitrary threshold voltage controlled by an external system to output a digital signal of either '1' or '0'. Next, a counter may count a number of times '1' occurs, and output the counted number as a digital type.

Since the EHP is proportional to an energy of an entering X-ray photon, images of different energies may be concurrently obtained through an exposure of the polychromatic X-ray using a counter designated for each of several threshold voltages and for each energy based on the EHP.

Specifically, in this case, the X-ray sensing unit may generate the plurality of X-ray images corresponding to the plurality of energy bands using the polychromatic X-ray passing through an object.

A detailed configuration of the image obtaining unit 110 will be described below with reference to FIGS. 3 and 4.

The first processing unit 120 may generate a plurality of material images using the generated plurality of X-ray images. According to an example embodiment, the material image may be an image about water, fat, protein, ash, etc.

A detailed configuration of the first processing unit 120 will be described below with reference to FIG. 8.

The second processing unit 130 may generate a high contrast X-ray image using at least one of the plurality of material images provided from the first processing unit 120.

The high contrast X-ray image may be a characteristic image calculating an abnormality of an outlier part using a ratio for each material, and displaying the calculated abnormality. In this instance, the outlier part may be a part in which a ratio between materials is outside a known normal range.

According to an example embodiment, the characteristic image may be an image in which the abnormality is expressed by a difference of either color or brightness. However, the present disclosure is not limited thereto, and the characteristic image may be an image expressed by discriminating either color or brightness of a part where the particular degree exceeds a predetermined threshold value from remaining parts.

According to another example embodiment, the high contrast X-ray image may be an anatomical image having a high contrast for each organ of a human body.

According to an example embodiment, to generate the anatomical image, the second processing unit 130 may perform an independent component analysis using a pixel value of at least two material images of the plurality of material images to thereby obtain at least two independent component images, and combine the at least two independent component images to generate the high contrast X-ray image.

According to another example embodiment, when generating the characteristic image, the second processing unit 130 may quantitatively express a degree in which a ratio between materials is outside a known normal range to thereby generate the characteristic image used for identifying the outlier part.

A detailed process of generating the high contrast X-ray image using the plurality of material images in the second processing unit 130 will be described below with reference to FIG. 9.

According to another example embodiment, an image processing apparatus 100 includes a third processing unit (not shown) instead of including the first processing unit 120 and the second processing unit 130. The third processing unit may perform an independent component analysis using a pixel value of at least two images of the plurality of X-ray material images generated by the image obtaining unit without using the material image to thereby obtain at least two independent component images, and combine the at least two independent component images to thereby generate the high contrast X-ray image. This will be described in detail below with reference to FIGS. 7 and 9.

The display unit 140 may visually display the high contrast X-ray image provided by the second processing unit 130. The display unit 140 may be an image device including a liquid crystal display (LCD) panel. However, this may be merely an example, and a configuration of the display unit 140 may be diversely utilized in electric equipment, printing equipment, etc.

Figure 2:
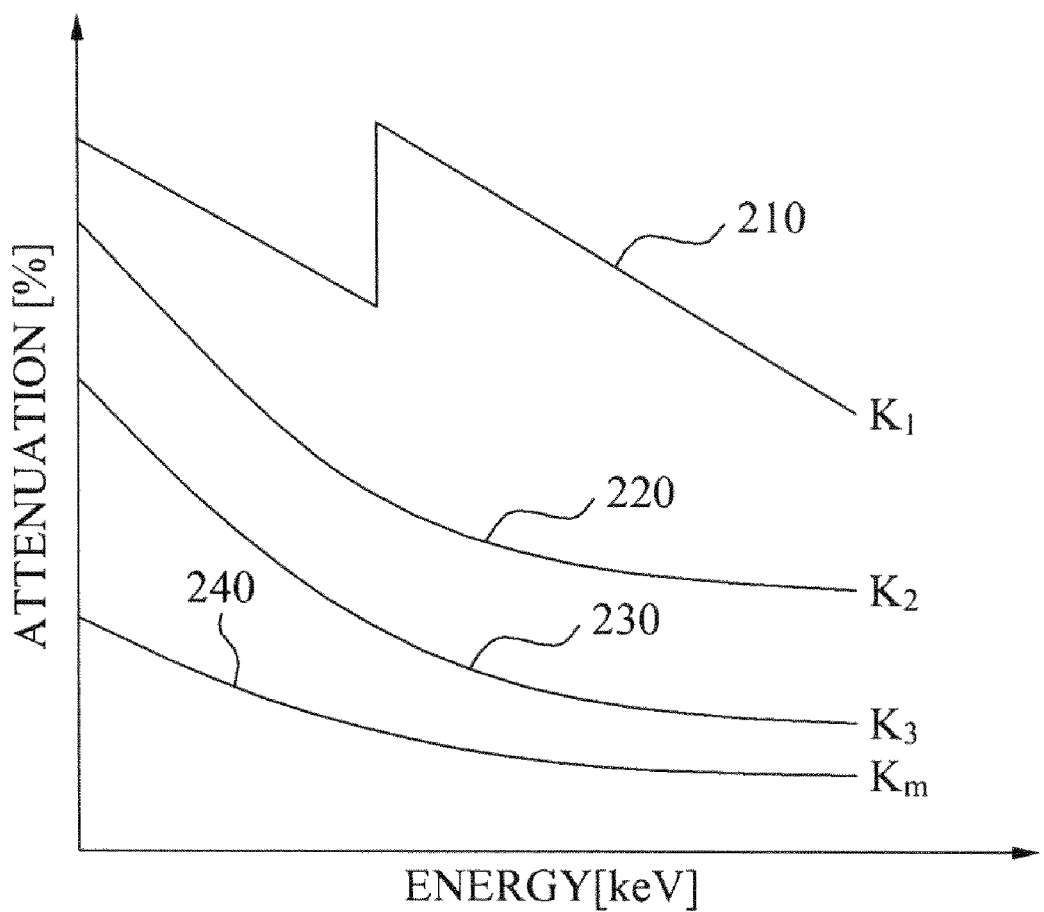
FIG. 2 illustrates an exemplary graph of an X-ray attenuation coefficient for each material in accordance with an energy band of an X-ray.

FIG. 2 illustrates an exemplary graph of an X-ray attenuation coefficient for each material in accordance with an energy band of an X-ray.

An X-axis of the graph may designate an energy of the X-ray. The X-ray having a greater energy value may have a shorter wavelength. A Y-axis of the graph may designate an attenuation coefficient.

Each of attenuation coefficient curved lines 210 to 240 may designate the X-ray attenuation coefficient of materials $K_1$ to $K_m$ in accordance with an increase in the energy of the X-ray. As shown in the curved lines 210 to 240, a transmittance may increase and the attenuation coefficient may be reduced along with an increase in the energy of the X-ray.

However, any material may have an edge in which the X-ray attenuation coefficient is reduced and then rapidly increases in a specific energy band along with the increase in the energy of the X-ray. For example, in a case of the curved line 210, there exists an edge with a rapid change in the attenuation coefficient of the X-ray. In general, the edge may be referred to as a K-edge, in which an attenuation coefficient of a photon may rapidly increase in a photon energy that slightly exceeds a bonding energy of a K shell of an electron within an atom mutually reacting with the photon.

Since the curved lines 210 to 240 of the materials $K_1$ to $K_m$ may show their unique attenuation coefficients, material images may be obtained using a plurality of X-ray images corresponding to multiple monochromatic bands.

Figure 3A:
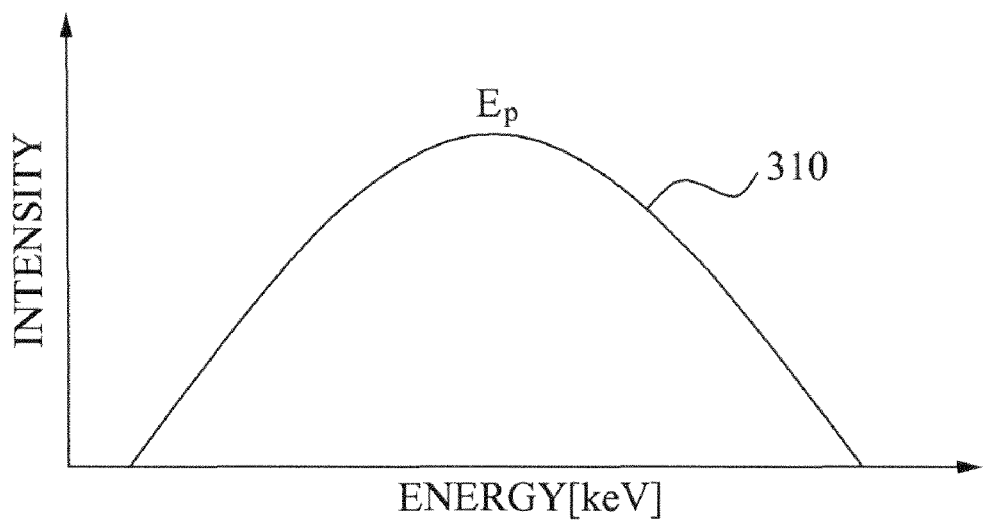
FIG. 3A and FIG. 3B illustrates energy distributions of a polychromatic X-ray and a monochromatic X-ray, respectively.
Figure 3B:
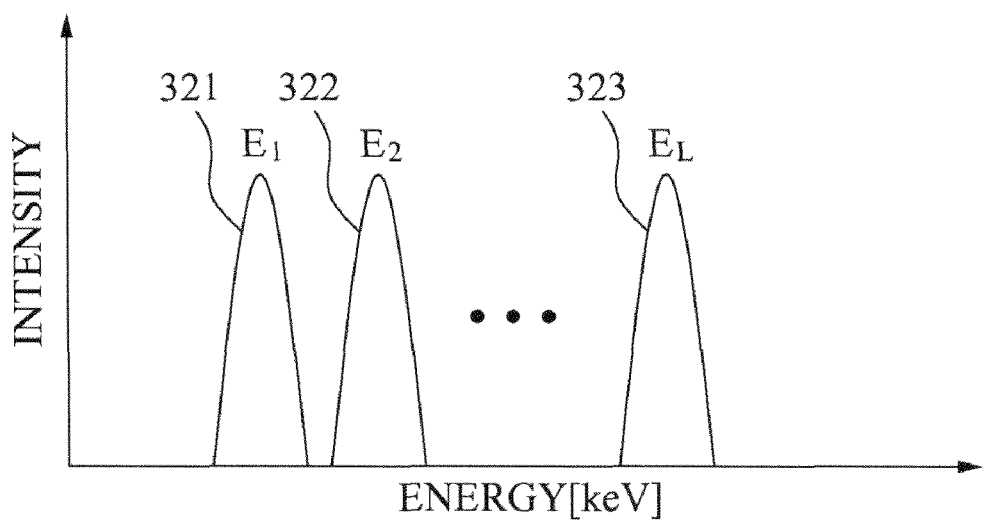

FIG. 3A and FIG. 3B are graphs illustrating energy distributions of a polychromatic X-ray and a monochromatic X-ray, respectively.

A curved line 310 of FIG. 3A may designate an energy distribution of a polychromatic X-ray. An X-ray generated in an X-ray generation device may have various energies. An X-ray image obtained by emitting the polychromatic X-ray through an object and by sensing the emitted X-ray via the X-ray sensing unit, for example, an X-ray film or an electronic X-ray sensing device, may have a relative contrast, particularly, in soft tissues. Accordingly, the obtained X-ray image may have poor effectiveness for purposes of medical use or security inspection.

According to an example embodiment, by emitting each of multiple monochromatic X-rays illustrated in FIG. 3B through an object, a plurality of X-ray images corresponding to energy bands being different from each other may be obtained.

Curved lines 321 to 323 of FIG. 3B may designate energy bands of $E_1$ to $E_L$, L being a natural number.

According to an example embodiment, an X-ray having an energy distribution of the curved line 310 of FIG. 3A may be filtered using a bandpass filter through which only an X-ray corresponding to a specific energy band selectively passes, thereby generating multiple monochromatic X-rays having energy distributions of the curved lines 321 to 323.

According to an example embodiment, the above-described filtering performed using the bandpass filter may be performed using a tunable filter. However, the present disclosure is not limited thereto, and the above described filtering may be performed using a plurality of filters through which different energy bands pass.

According to another example embodiment, the X-ray having the energy distribution of the curved line 310 of FIG. 3A may enter in a crystal slit having a uniform lattice by a predetermined angle, so that the entering X-ray may be divided into X-rays of different energy bands such as the curved lines 321 to 323 of FIG. 3B. A detailed description of the present example embodiment will be given below with reference to FIG. 4.

Figure 4:
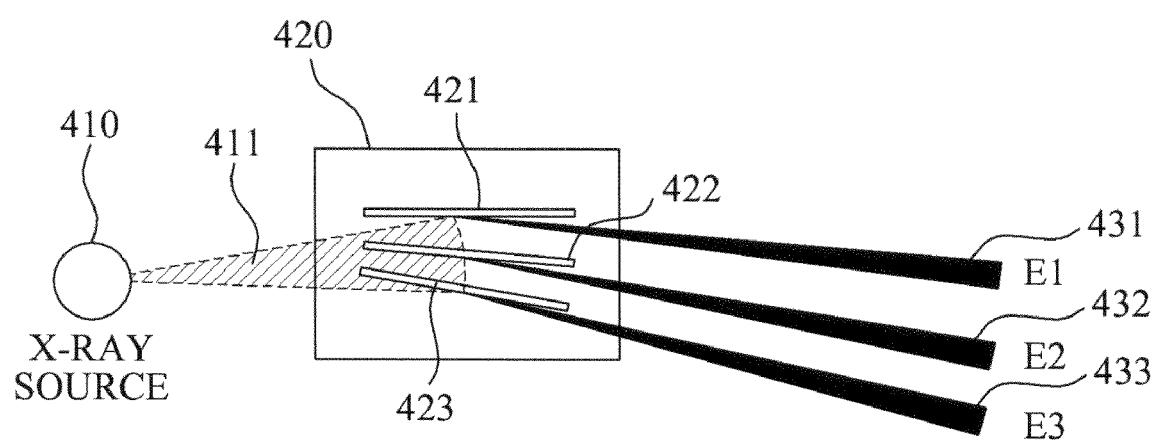
FIG. 4 illustrates a monochromatic X-ray generation apparatus according to example embodiments.

FIG. 4 illustrates a monochromatic X-ray generation apparatus according to example embodiments.

An X-ray source 410 may generate a polychromatic X-ray 411 having a polychromatic energy distribution such as the curved line 310 of FIG. 3A, and emit the generated polychromatic X-ray 411.

A spectroscopic unit 420 may have a plurality of slits 421 to 423, and each of the slits may have a uniform lattice and may be disposed with a different angle.

When being reflected on each of the slits 421, 422, and 423, the polychromatic X-ray 411 may be divided into monochromatic X-rays 431, 432, and 433, having different energy bands in accordance with each angle of the slits. Such division of the polychromatic X-ray 411 may relate to Bragg's theory.

Since an existing X-ray source 410 generating the polychromatic X-ray 411 using the spectroscopic unit 420 is used as is, miniaturization of a device may be realized, and the multiple monochromatic X-rays may be generated with a relatively low cost.

When obtaining X-ray images with respect to an object using each of the X-rays 431 to 433 of the different energy bands, a plurality of X-ray images corresponding to each of the different energy bands may be obtained. Example embodiments for the above-described process will be described below in detail with reference to drawings.

According to another example embodiment, images corresponding to X-rays of different energy bands such as the curved lines 321 to 323 of FIG. 3B may be obtained through the X-ray having the energy distribution of the curved line 310 of FIG. 3A using an X-ray detector having an energy discrimination function.

Figure 5:
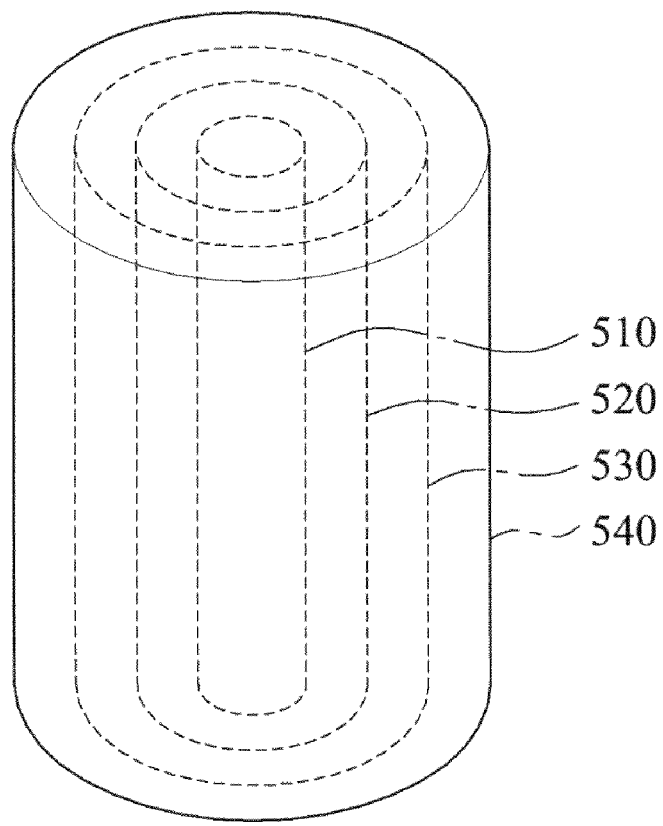
FIG. 5 illustrates a conceptual diagram of an exemplary human body configuration that is analyzed as a high contrast X-ray image through an image processing method according to example embodiments.

FIG. 5 is a conceptual diagram of an exemplary human body configuration that is analyzed as a high contrast X-ray image through an image processing method according to example embodiments.

A part 500 of a human body may be configured of ash 510, protein 520, water 530, and fat 540. However, a configuration of FIG. 5 is merely an example and may be different from an actual human body tissue.

When obtaining an X-ray image with respect to the part 500 of the human body using the polychromatic X-ray having the energy distribution of the curved line 310 of FIG. 3A, a discrimination between ash 510 and other configurations may be significantly shown, however, a discrimination between protein 520, water 530, and fat 540, hereinafter, referred to as 'soft tissues', may be insignificantly shown.

However, according to an example embodiment, the plurality of X-ray images corresponding to each of the different energy bands with respect to the part 500 may be obtained using the multiple monochromatic X-ray having the energy distributions of the curved lines 321 to 323 of FIG. 3B, the obtained X-ray images may be processed to generate material images, and a high contrast X-ray image may be obtained using the material images, whereby the discrimination between the soft tissues may be significantly shown.

Figure 6:
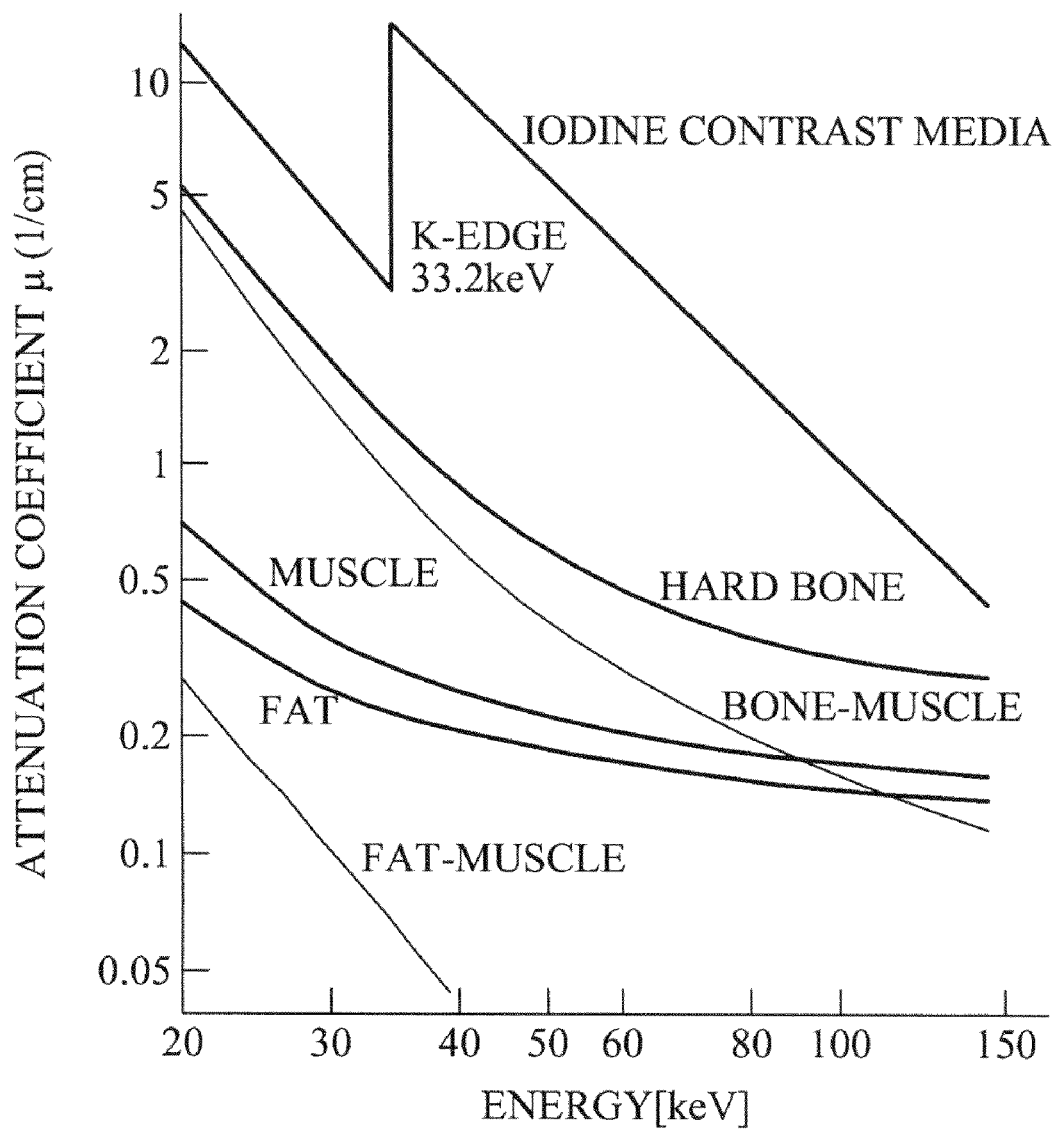
FIG. 6 illustrates an exemplary graph of an X-ray attenuation coefficient for each material constituting a human body.

FIG. 6 is an exemplary graph of an X-ray attenuation coefficient for each material constituting a human body.

In the graph, a curved line of an attenuation coefficient with respect to each of hard bone, muscle, and fat may be illustrated, an attenuation coefficient difference between hard bone and muscle and an attenuation coefficient difference between fat and muscle are illustrated.

Also, an attenuation coefficient-curved line of a specific material having a K-edge such as Iodine is illustrated in the graph. The Iodine contrast media may be a material utilized in photographing a blood vessel and the like due to the K-edge.

Figure 7:
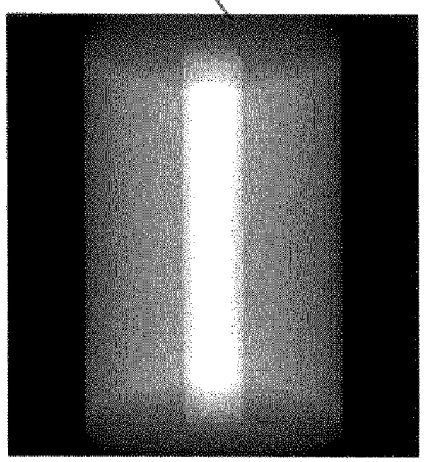
FIG. 7 illustrates a plurality of X-ray images obtained by photographing an exemplary human body configuration, for example, the exemplary human body configuration of FIG. 5, using a multiple monochromatic X-ray, according to example embodiments.
Figure 7:
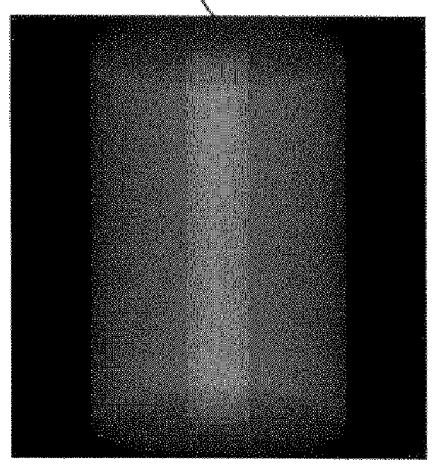
Figure 7:
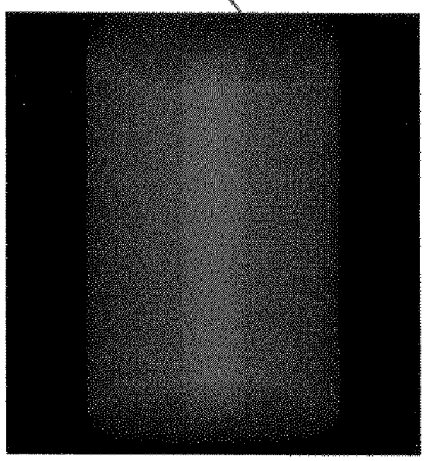
Figure 7:
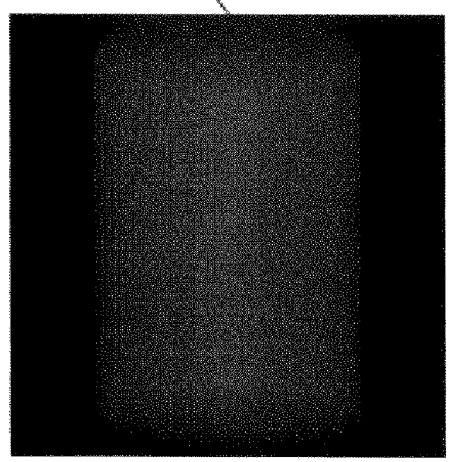

FIG. 7 illustrates a plurality of X-ray images obtained by photographing an exemplary human body configuration, for example, the human body configuration of FIG. 5, using a multiple monochromatic X-ray, according to example embodiments.

An image 710 may be an image obtained by photographing the part 500 of the human body using an X-ray corresponding to an energy band around 20 Kiloelectronvolt (KeV). An image 720 may be an image obtained using an X-ray corresponding to an energy band around 25 KeV. Also, images 730 and 740 may be images obtained using X-rays corresponding to energy bands in the vicinity of 30 KeV and 40 KeV, respectively.

As illustrated in FIG. 2, an image obtained using an X-ray corresponding to a relatively higher energy band may show an insignificant discrimination between materials. This is because a difference of an X-ray attenuation coefficient between the materials may be reduced along with an increase in the energy of the X-ray.

Using the plurality of images 710 to 740, as an example, a process of obtaining an X-ray for each material will be described in detail with reference to FIG. 8.

Figure 8:
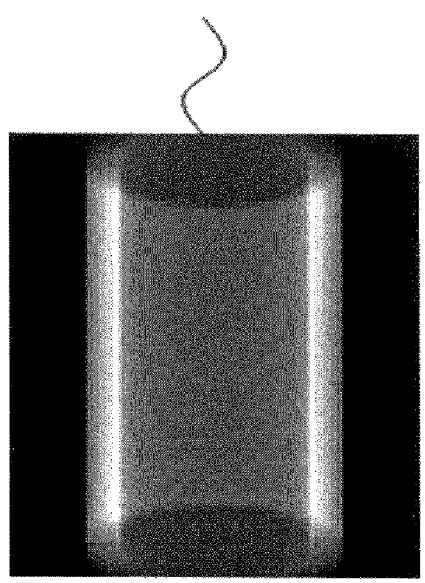
FIG. 8 illustrates a plurality of material images generated using the plurality of X-ray images, for example, the plurality of X-ray images of FIG. 7, according to example embodiments.
Figure 8:
Figure 8:
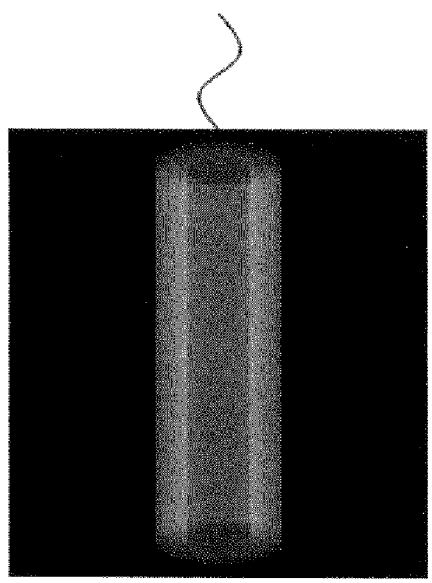
Figure 8:
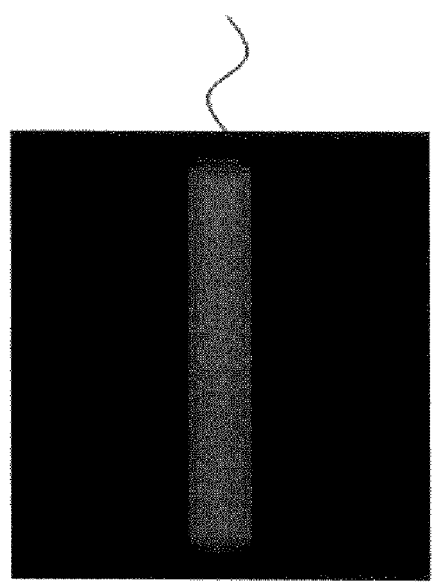

FIG. 8 illustrates a plurality of material images generated using the plurality of X-ray images of FIG. 7, according to example embodiments.

According to an example embodiment, material images 810 to 840 may be generated using a plurality of images, for example, the plurality of images 710 to 740 corresponding to each of the different energy bands of FIG. 7.

Hereinafter, the monochromatic energy band will be assumed to be an approximate single energy E. When an attenuation coefficient of an X-ray being comprised of $N_0$-numbered photons having the single energy E is (E), a number N of the photons after passing through an object having a thickness T may be expressed, for example as Equation 1, shown below.

$$N = N_0 e^{-\mu(E)T}.$$  Equation 1

When a thickness of an m-th material is $T_m$ in a case where a number of types of materials through which the X-ray passes is M, Equation 1 may be re-expressed, for example, as Equation 2, shown below.

$$N = N_0 e^{-(\mu_1(E)T_1 + \mu_2(E)T_2 + \ldots + \mu_M(E)T_M)}$$  Equation 2

An image pixel value may be determined by diving both members of Equation 2 by a measurable $N_0$ and using –log. In the same manner, when L-numbered X-ray images are obtained with respect to L different energies of $E_1, E_2, \ldots, E_l, \ldots, E_L$, a value $I(E_l)$ of a pixel may be expressed, for example, as Equation 3, shown below.

$$I(E_l) = -\log(N(E_l)/N_0)$$  Equation 3
$$= \mu_1(E_l)T_1 + \mu_2(E_l)T_2 + \ldots + \mu_M(E_l)T_M.$$

Accordingly, L numbered-equations with respect to each pixel, as shown in Equation 3, may be obtained from the L numbered-monochromatic X-ray images, and this will be expressed as a determinant, for example, as in Equation 4, shown below.

$$I = \mu \cdot T.$$  Equation 4

Accordingly, when L=M, divided images for each material may be obtained by calculating a matrix operation of $T = \mu^{-1} \cdot I$. Equation 4 may be obtained when an ideal monochromatic X-ray image is assumed, however, Equation 4 may be changeable when using a Quasi-monochromatic X-ray image having a certain bandwidth.

A number L of the monochromatic X-ray images obtained and illustrated in FIG. 7 is 4 (L=4), and a number M of materials intended to be divided and expressed is 4 (M=4). Accordingly, using Equations 1 to 4, the four material images 810 to 840 may be generated.

The material image 810 may be an image expressed by dividing the fat, and the material images 820 to 840 may be images expressed by dividing water, protein, and hard bone, respectively.

Figure 9:
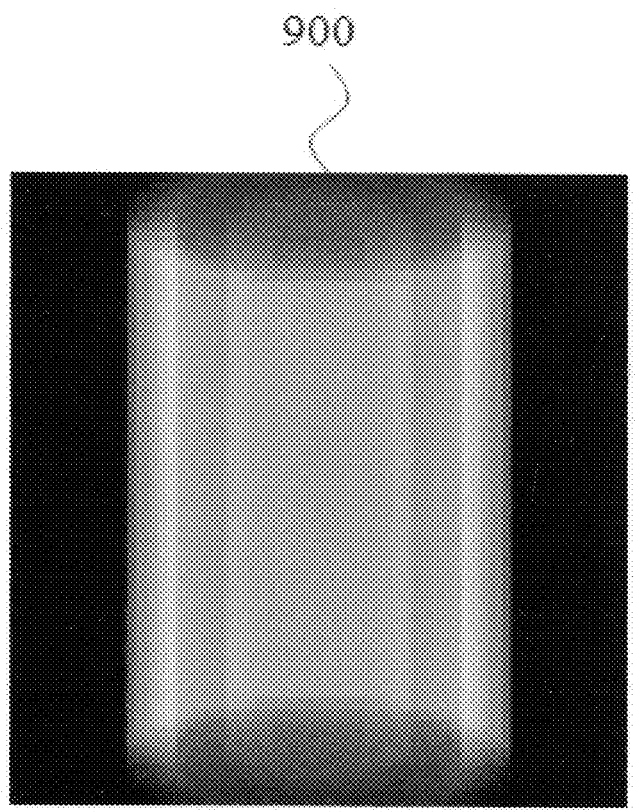
FIG. 9 illustrates a high contrast X-ray image with respect to an exemplary human body configuration, for example the exemplary human body configuration of FIG. 5 generated using a plurality of material images, for example, the plurality of material images of FIG. 8, according to example embodiments.

FIG. 9 illustrates a high contrast X-ray image with respect to an exemplary human body configuration, for example, the exemplary human body configuration of FIG. 5 generated using the plurality of material images of FIG. 8, according to example embodiments.

When the material images 810 to 840 of FIG. 8 are obtained, the material images 810 to 840 may be re-configured to suit their purposes, thereby generating a high contrast X-ray image.

Fields in which example embodiments of the present disclosure are utilized may be varied. As examples of the fields, a security inspection field, a medical diagnosis field using a medical image, etc., may be given. In the security inspection field, the material images may be used as are for a main purpose of searching for a specific material, or characteristic images using a ratio between materials may be generated and used.

Also, in the medical diagnosis field, the characteristic image obtained when an outlier part in which a ratio difference between the materials is outside a known normal range is distinguished as an abnormal tissue, and an anatomical image obtained by anatomically expressing organs of the human body because of a high contrast even in soft tissues as well as hard tissues may be used.

According to an example embodiment, the characteristic image may be generated using the material images 810 to 840 (FIG. 8), based on a different material component ratio between normal tissues and abnormal tissues, for example, lesioned tissue such as cancerous tissue, fatty liver, etc.

For example, in a case of a liver, there may be generated an image expressing a risk of a fatty liver level using a ratio of the fat component to overall components of the liver due to a basic ratio of a normal fat component of 3%. This will be implemented by comparing and calculating the pixel values for each material as illustrated in FIG. 8.

According to another example embodiment, an anatomical image 900 may be expressed using the material images 810 to 840 (FIG. 8). The anatomical image may be an image visually showing shapes of organs of the human body. The anatomical image may have effects in that a discrimination between the organs is significantly shown, and the human body appears to be penetrated.

Four components of water, fat, protein, and hard bone may occupy 90% or more of the human body. According to the present example embodiment, the material images may be re-configured as the anatomical images using a material component ratio of organs, such as a heart, a stomach, a liver, lungs, etc., and be statistically obtained when it is assumed that each organ has a unique material component ratio. A specific numeral value of the material component ratio may vary depending on individuals; however, statistical representative values may be used.

In this case, Equation 5 below, for example, may be satisfied between the material images 810 to 840 and the anatomical image 900.

$$T(p) = \sum_{n=1}^{N} O_n(p) \cdot R(O_n).$$  Equation 5

Here, N represents a number of types of materials providing material component ratio information in the anatomical image, T(p) represents a material image vector $[T_1, T_2, \ldots, T_m, \ldots, T_M]^T$ in a pixel p, $T_m$ represents a pixel value of an m-th material image, $O_n(p)$ represents a thickness of an n-th organ image in the pixel p, and $R(O_n)$ represents a material component ratio $[R_1(O_n), R_2(O_n), \ldots, R_m(O_n), \ldots, R_M(O_n)]^T$ of the n-th organ.

Here, $R_m(O_n)$ represents a relative amount of the m-th material of the n-th organ image. The material image vector may be expressed in a linear bonding type of the material component ratio for each organ, using the thickness of the organ image as a coefficient. As described above, as for the material component ratio, when $R(O_n)$ is specified using an average value statistically having universality, the determinant of Equation 5 may have a unique answer.

Otherwise, when the material component ratio having a slight declination by individuals is considered, the determinant of Equation 5 may not have the unique answer due to a non-specific $R(O_n)$. In this case, when it is assumed that $O_n(p)$ is a signal mixed by an independent signal with respect to n, Equation 5 may be regarded as an independent component analysis expressed by, for example, Equation 6, shown below.

$$x = A\,s, \quad \text{Equation 6}$$

wherein $x=[T_1, T_2, \ldots, T_M]^T$, $S=[O_1, O_2, \ldots, O_N]^T$, and $A=[R(O_1), R(O_2), \ldots, R(O_N)]$. Accordingly, $O_n(p)$ and $R(O_n)$ may be determined using a statistical analysis with respect to T even without an accurate knowledge with respect to $R(O_n)$.

However, a pixel expressing the external air/space of an object not having any value from among the overall material images may be excluded when calculating. According to the present example embodiment, $O_n$ may denote an image divided for each organ, and thus a high contrast anatomical X-ray image may be generated.

In addition, Equation 7 below may be obtained when using an m-th element $T_m$ of $T(p)$ of Equation 5 in Equation 3.

$$I(E_l; p) = \sum_{m=1}^{M} \mu_m(E_l) T_m \quad \text{Equation 7}$$

$$= \sum_{m=1}^{M} \left[ \mu_m(E_l) \left\{ \sum_{n=1}^{N} O_n(p) \cdot R_m(O_n) \right\} \right]$$

$$= \sum_{n=1}^{N} \left[ O_n(p) \left\{ \sum_{m=1}^{M} \mu_m(E_l) \cdot R_m(O_n) \right\} \right].$$

In Equation 7, each pixel value $I(E_l;p)$ of a plurality of energy images may be expressed as a liner bonding of a unique constant of $$\sum_{m=1}^{M} \mu_m(E_l) \cdot R_m(O_n)$$

and a division image $O_n(p)$ for each organ.

Accordingly, an independent component analysis may be performed using the pixel value of the plurality of X-ray images for each energy obtained by the image obtaining unit 110 (FIG. 1) while omitting a process of obtaining the material images, thereby obtaining images divided for each organ.

Figure 10:
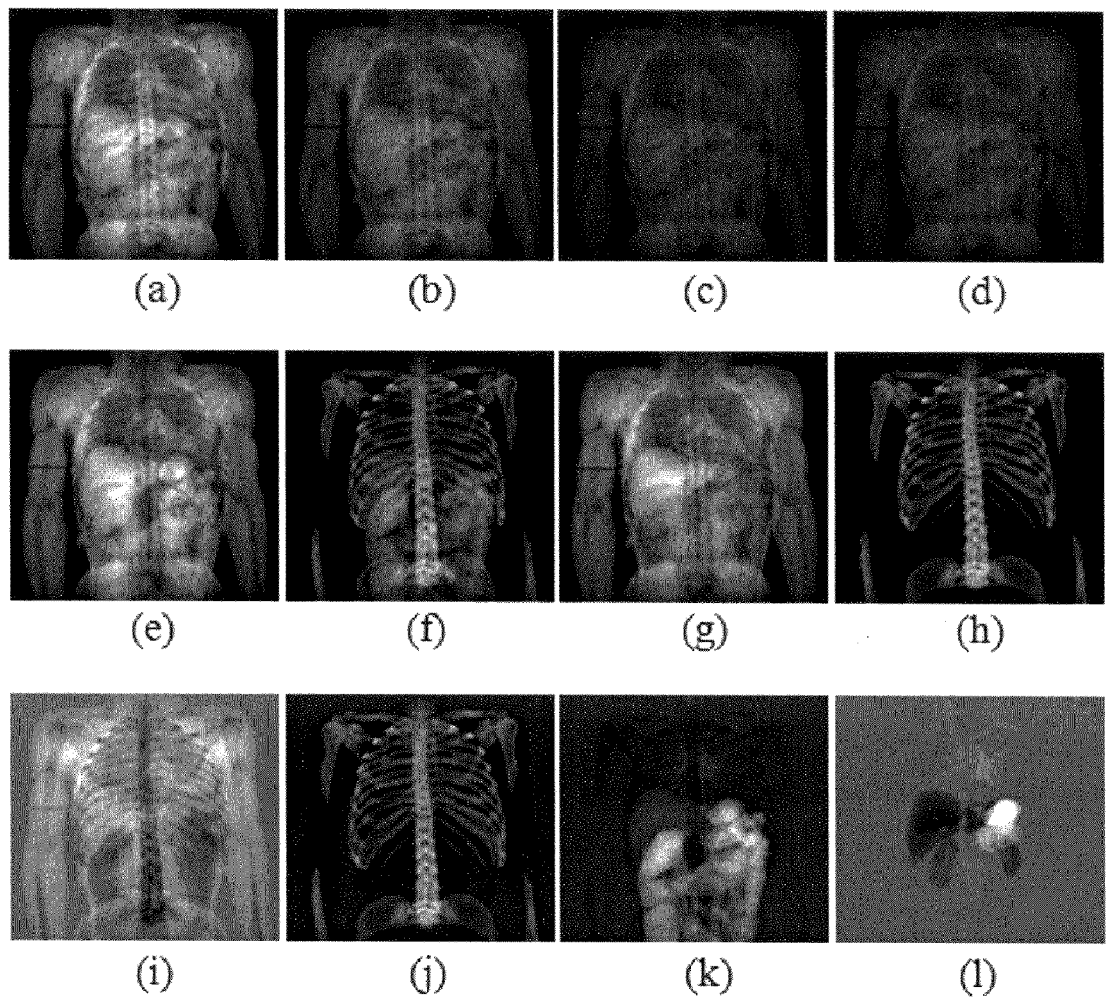
FIG. 10 illustrates a plurality of images generated as a result of an independent component analysis using a plurality of material images generated using a plurality of images for each energy, according to example embodiments.

FIG. 10 illustrates a plurality of images generated as a result of an independent component analysis using a plurality of material images generated using a plurality of images for each energy, according to example embodiments.

Images (a), (b), (c), and (d) of FIG. 10 may be monochromatic X-ray images obtained from different energies, and images (e), (f), (g), and (h) may be material images calculated using the images (a) to (d).

Also, images (i), (j) (k), and (l) may be images obtained as a result of the independent component analysis. Particularly, as illustrated in the images (i) to (l), by using the independent component analysis, overlapped organ structures may be divided and expressed, and thus a high contrast X-ray images through which shapes of organs are clearly observed in comparison with the images (a) to (d) may be generated.

By using the generated high contrast X-ray image, a high definition X-ray image with an improved visual recognition may be obtained, and a contrast medium, for example, the Iodine contrast media described with reference to FIG. 6, may not be used when photographing a blood vessel, thereby greatly reducing the risk of the patient.

Also, for example, only a characteristic image with respect to an abnormality in a component ratio of the fat within the liver may be considered, and thus the anatomical high contrast X-ray image may be highly appreciated in an image diagnosis of the medical diagnosis field.

Figure 11:
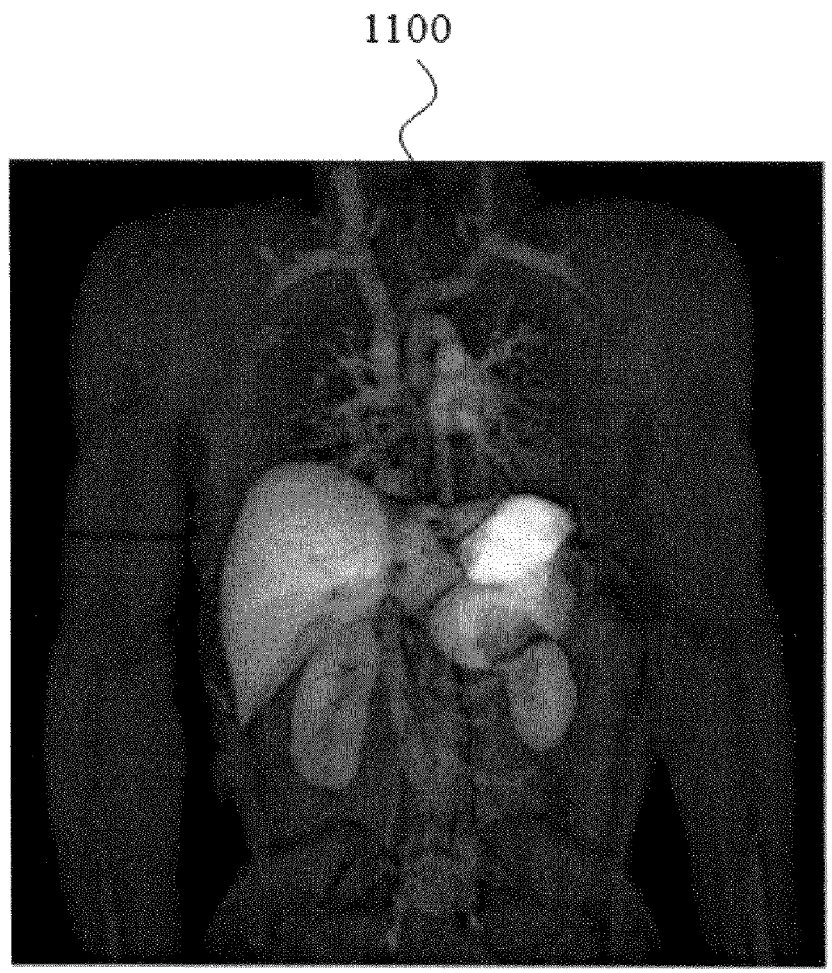
FIG. 11 illustrates a high contrast X-ray image of a human body generated according to example embodiments.

FIG. 11 illustrates a high contrast X-ray image 1100 of a human body generated according to example embodiments.

The high contrast X-ray image 1100 may be obtained in the above described processes, and a contrast with respect to the soft tissues in comparison with an existing X-ray image may be improved as illustrated in FIG. 11.

However, the high contrast X-ray image 1100 may be merely an exemplary image. Specifically, various types of images may be generated according to the image processing method of the present disclosure.

Also, an arbitrary anatomical image with an improved visual recognition may be obtained by expressing organs to have different colors for each organ.

Figure 12:
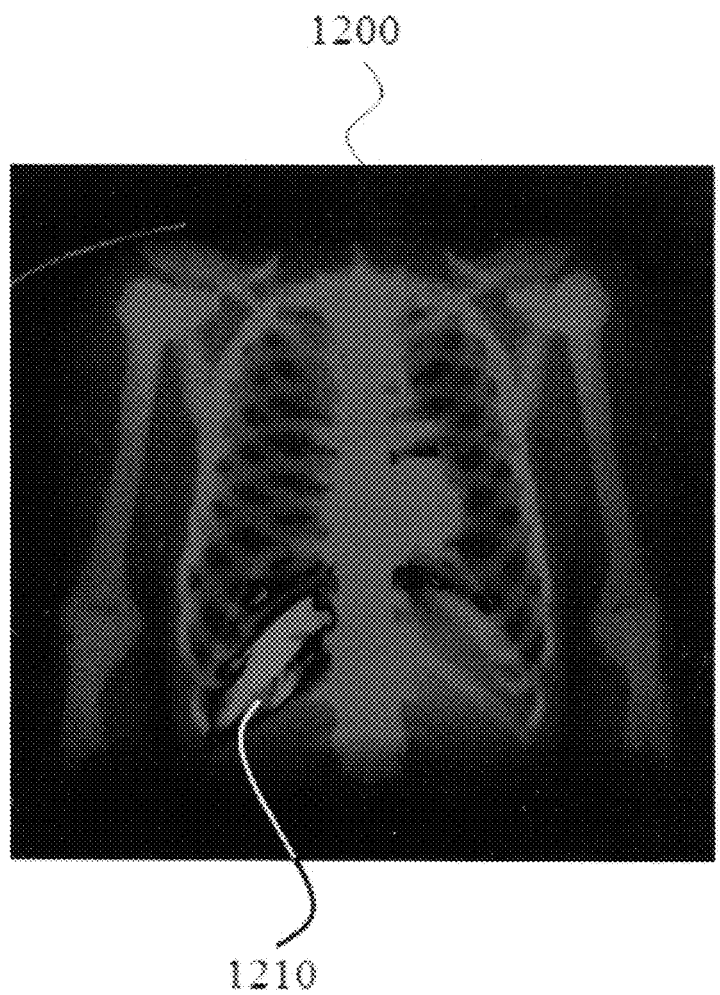
FIG. 12 illustrates a characteristic image of a human body generated according to example embodiments.

FIG. 12 illustrates a characteristic image of a human body generated according to example embodiments.

According to the present example embodiment, an outlier part 1210 may be discriminated and expressed using material image by discriminatingly expressing a color of a part in which a ratio of the fat exceeds a predetermined threshold value, for example, 3%, from those of other parts.

According to the present example embodiment, the color of the outlier part 1210 may be discriminately expressed from other parts, however, according to another example embodiment, a light and shade of the outlier part 1210 may be discriminately expressed.

Also, according to another example embodiment, there may be provided resultant images expressing an abnormality, that is, a degree in which the ratio of the fat is outside a known normal range using a difference between colors or light and shades, without separately extracting the outlier part. In this case, a value of the abnormality may be a value of light and shade of the resultant image.

Figure 13:
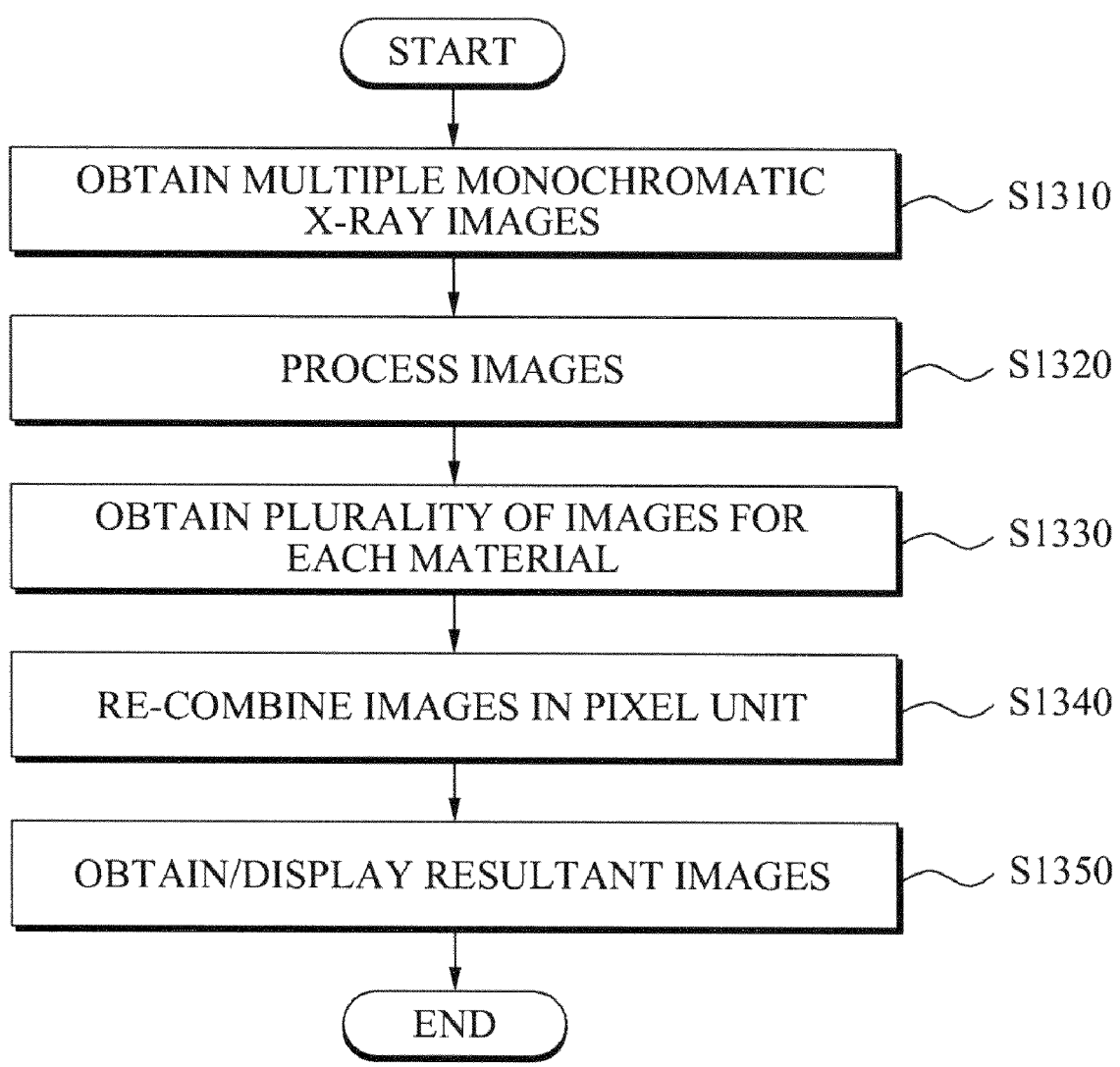
FIG. 13 illustrates a flowchart of an image processing method according to example embodiments.

FIG. 13 is a flowchart illustrating an image processing method according to example embodiments.

In operation S1310, a plurality of X-ray images may be obtained using multiple monochromatic X-rays corresponding to a plurality of energy bands being different from each other.

According to an example embodiment, in operation S1310, a polychromatic X-ray may be generated, and the generated polychromatic X-ray may be filtered, or may be reflected with different angles and divided, thereby generating the multiple monochromatic X-rays. The above described filtering and dividing processes are the same as descriptions of FIGS. 3 and 4.

The multiple monochromatic X-rays corresponding to the different energy bands may be emitted to an object, and the emitted X-rays may be sensed, whereby a plurality of X-ray images, for example, images 710 to 740 of FIG. 7, may be generated.

According to an example embodiment, in operation S1320, various post processes may be performed. For example, with respect to the plurality of X-ray images generated in operation S1310, the post processes such as a noise reduction, a contrast adjustment, and an edge enhancement may be performed. An image quality obtained through the image processing method in subsequent operations may be improved through these post processes and is generally referred to as an image processing.

In operation S1330, a plurality of material images may be obtained. Operation S1330 may be performed using Equations 1 to 4, and a more detailed process may be the same as the description of FIG. 8. However, according to another example, when the high contrast X-ray image is obtained using the plurality of X-ray images, that is, when a process of obtaining the material images is omitted, operation S1330 will be omitted.

In operation S1340, the images may be re-combined in a pixel unit, thereby obtaining the high contrast X-ray image.

According to an example embodiment, the high contrast X-ray image may be the characteristic images. However, according to another example embodiment, the high contrast X-ray image may be the anatomical image.

In each case, a detailed process of re-combining the images in the pixel unit may be the same as the descriptions of FIG. 9 using Equations 5 to 6.

Also, the process of re-combining the images performed when the process of obtaining the material images is omitted and the high contrast X-ray image is obtained from the plurality of X-ray images may be the same as the descriptions of FIG. 7.

In operation S1350, the high contrast X-ray image may be displayed. As described above, in operation S1350, the color or light and shade of each organ may be discriminately expressed, or in a case of the characteristic images, the color or light and shade of the outlier part may be discriminately expressed.

Figure 14:
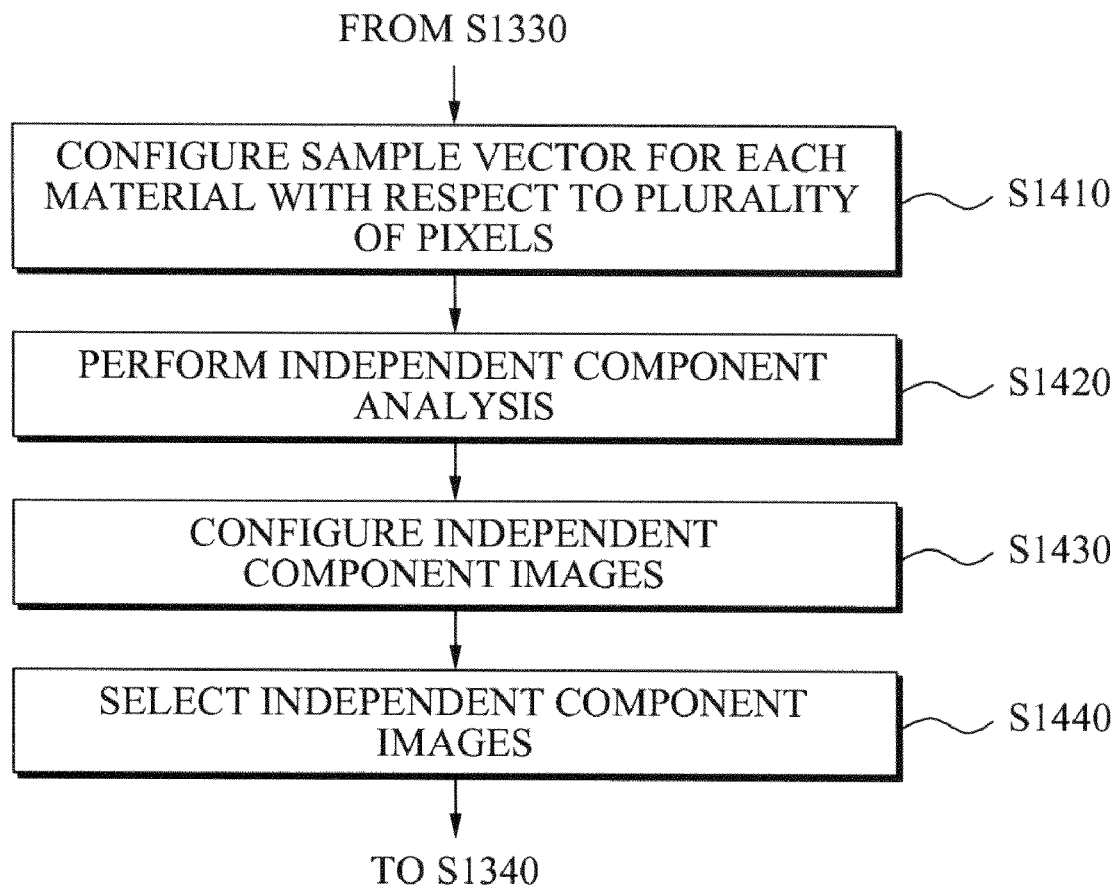
FIG. 14 illustrates a flowchart of a process of generating a high contrast X-ray image using a plurality of material images in an image processing method according to example embodiments.

FIG. 14 is a flowchart illustrating an image processing method performed after operation S1330 of FIG. 13 so as to generate the anatomical high contrast X-ray image using the plurality of material images in the image processing method according to example embodiments.

In operation S1410, the material images obtained in operation S1330 may be analyzed to thereby configure a sample vector, that is, T(p) of Equation 5, for each material with respect to a plurality of pixels.

In operation S1420, the independent component analysis of Equation 6 may be performed, and in operation S1430, the independent component image corresponding to $O_n(p)$ may be configured, thereby generating component images for each organ. Specifically, $O_n(p)$ and $R(O_n)$ of Equation 6 may be determined. In operation S1440, only component images being suitable for final images from among the component images for each organ may be selected.

In addition to the above described embodiments, embodiments can also be implemented through computer readable code/instructions in/on a medium, e.g., a computer readable medium, to control at least one processing device to implement any above described embodiment. The medium can correspond to any medium/media permitting the storing and/or transmission of the computer readable code.

The computer readable code can be recorded on a medium in a variety of ways, with examples of recording media including magnetic storage media (e.g., ROM, floppy disks, hard disks, etc.) and optical recording media (e.g., CD-ROMs, or DVDs). The computer readable code may also be transferred through transmission media as well as elements of the Internet, for example. Thus, the medium may be such a defined and measurable structure carrying or controlling a signal or information, such as a device carrying a bitstream, for example, according to one or more embodiments. The media may also be a distributed network, so that the computer readable code is stored/transferred and executed in a distributed fashion. Still further, as only an example, the processing device could include a processor or a computer processor, and processing elements may be distributed and/or included in a single device.

Although a few example embodiments have been shown and described, the present disclosure is not limited to the described example embodiments. Instead, it would be appreciated by those skilled in the art that changes may be made to these example embodiments without departing from the principles and spirit of the disclosure, the scope of which is defined by the claims and their equivalents.

What is claimed is:

1. An image processing apparatus, comprising:
   an image obtaining unit to obtain a plurality of X-ray images using a plurality of X-rays corresponding to each of a plurality of energy bands being different from each other;
   a first processing unit to generate a plurality of material images using the plurality of X-ray images; and
   a second processing unit to generate a high contrast X-ray image using at least one of the plurality of material images.

2. The image processing apparatus of claim 1, wherein the image obtaining unit includes:
   an X-ray generation unit to generate a polychromatic X-ray;
   a filtering unit to filter the polychromatic X-ray to provide the plurality of X-rays corresponding to each of the plurality of energy bands; and
   an X-ray sensing unit to sense the plurality of X-rays corresponding to each of the plurality of energy bands passing through the filtering unit to thereby obtain the plurality of X-ray images.

3. The image processing apparatus of claim 1, wherein the image obtaining unit includes:
   an X-ray generation unit to generate a polychromatic X-ray;
   a spectroscopic unit to refract the polychromatic X-ray to thereby divide the refracted polychromatic X-ray into the plurality of X-rays corresponding to each of the plurality of energy bands; and
   an X-ray sensing unit to sense the plurality of X-rays corresponding to each of the plurality of energy bands passing through the spectroscopic unit to thereby obtain the plurality of X-ray images.

4. The image processing apparatus of claim 1, wherein the image obtaining unit includes:
   an X-ray generation unit to generate a polychromatic X-ray; and
   an X-ray sensing unit to obtain the plurality of X-ray images corresponding to each of the plurality of energy bands, using the polychromatic X-ray.

5. The image processing apparatus of claim 1, wherein the first processing unit selects at least m X-ray images, m being a natural number, from among the plurality of X-ray images, and analyzes the selected m X-ray images in a pixel unit to generate m material images.

6. The image processing apparatus of claim 5, wherein the second processing unit performs an independent component analysis using a pixel value of at least two material images from among the m material images to thereby obtain at least one independent component image, and combines the independent component images to thereby obtain the high contrast X-ray image.

7. The image processing apparatus of claim 6, wherein the second processing unit performs at least one post processing of a noise reduction, a contrast adjustment, and an edge enhancement before performing the independent component analysis.

8. The image processing apparatus of claim 5, wherein the second processing unit generates a characteristic image in which an outlier part is identified, using at least two material images from among the m material images, the outlier part being a part in which a ratio between materials is outside a known normal range.

9. The image processing apparatus of claim 5, wherein the m material images include a water image, a fat image, a protein image, and an ash image.

10. The image processing apparatus of claim 9, wherein the second processing unit identifies a part in which a ratio of water and fat is outside a known normal range as an outlier part using the water image and the fat image, and discriminates at least one of a color and shade of the outlier part from other parts to thereby generate a characteristic image.

11. An image processing apparatus, comprising:
    an image obtaining unit to obtain a plurality of X-ray images using a plurality of X-rays corresponding to each of a plurality of energy bands being different from each other; and
    a third processing unit to perform an independent component analysis using a pixel value of at least two X-ray images from among the plurality of X-ray images to thereby obtain at least one independent component image, and to combine the at least one independent component image to thereby generate a high contrast X-ray image.

12. An image processing method, comprising:
    obtaining a plurality of X-ray images using a plurality of X-rays corresponding to each of a plurality of energy bands being different from each other;
    generating a plurality of material images using the plurality of X-ray images; and
    generating a high contrast X-ray image using at least one of the plurality of material images.

13. The image processing method of claim 12, wherein the obtaining includes:
    generating a polychromatic X-ray;
    filtering the polychromatic X-ray to provide the plurality of X-rays corresponding to each of the plurality of energy bands; and
    sensing a plurality of X-rays corresponding to each of the filtered plurality of energy bands to obtain the plurality of X-ray images.

14. The image processing method of claim 12, wherein the generating of the plurality of material images includes:
    selecting at least m X-ray images, m being a natural number, from among the plurality of X-ray images; and
    analyzing the selected at least m X-ray images in a pixel unit to generate m material images.

15. The image processing method of claim 14, wherein the generating of the high contrast X-ray image includes:
    performing an independent component analysis using a pixel value of at least one material image from among the generated m material images; and
    combining at least one independent component image obtained through the independent component analysis to generate the high contrast X-ray image.

16. The image processing method of claim 14, wherein the generating of the high contrast X-ray image includes:
    calculating an abnormality of an outlier part in which a ratio between materials is outside a known normal range, using at least two material images from among the generated m material images; and
    adjusting a color or brightness value of the calculated outlier part to obtain an image identified as the outlier part.

17. The image processing method of claim 14, wherein the m material images include a water image, a fat image, a protein image, and an ash image.

18. The image processing method of claim 17, wherein the generating of the high contrast X-ray image includes:
    detecting a outlier part in which a ratio of water and fat is outside a known normal range using the water image and the fat image; and
    adjusting a color and brightness value of the detected outlier part to generate an image identified as the outlier part.

19. At least one medium comprising computer readable instructions causing at least one processing device to implement the method of claim 12.

20. An image processing method, comprising:
    obtaining a plurality of X-ray images using a plurality of X-rays corresponding to each of a plurality of energy bands;
    performing an independent component analysis using pixel values of at least two X-ray images from among the obtained plurality of X-ray images; and
    combining at least two independent component images obtained through the independent component analysis to thereby generate a high contrast X-ray image.

21. At least one medium comprising computer readable instructions causing at least one processing device to implement the method of claim 20.

* * * * *